United States Patent
Jin et al.

(10) Patent No.: US 9,522,967 B2
(45) Date of Patent: Dec. 20, 2016

(54) PHOTOPOLYMERIZABLE COMPOSITIONS FEATURING NOVEL AMINE ACCELERATOR FOR IMPROVED COLOR STABILITY AND REDUCED POLYMERIZATION STRESS THEREBY

(75) Inventors: Xiaoming Jin, Middletown, DE (US); Paul D. Hammesfahr, Wyoming, DE (US)

(73) Assignee: DENTSPLY International Inc., York, PA (US)

( * ) Notice: Subject to any disclaimer, the term of this patent is extended or adjusted under 35 U.S.C. 154(b) by 406 days.

(21) Appl. No.: 11/811,137

(22) Filed: Jun. 8, 2007

(65) Prior Publication Data

US 2008/0306179 A1   Dec. 11, 2008

Related U.S. Application Data (60) Provisional application No. 60/812,658, filed on Jun. 9, 2006.

(51) Int. Cl.
*C08F 2/50*   (2006.01)

(52) U.S. Cl.
CPC ....................... *C08F 2/50* (2013.01)

(58) Field of Classification Search
CPC ................................ C08F 2/50; C09D 155/00
(Continued)

(56) References Cited

U.S. PATENT DOCUMENTS 4,205,988 A * 6/1980 Ozaki et al. .................. 430/340
4,234,399 A 11/1980 McDowell et al.
(Continued)

FOREIGN PATENT DOCUMENTS

WO   WO 97/35837   10/1997

OTHER PUBLICATIONS

Sakamoto et al., "Light as a sconstruction tool of metal nanoparticles: Synthesis and mechanism" Nov. 26, 2008. J. Photochem Rev. 10; 33-56.*

(Continued)

*Primary Examiner* — Michael Pepitone
*Assistant Examiner* — Jessica Roswell
(74) *Attorney, Agent, or Firm* — Leana Levin; Douglas J. Hura; David A. Zdurne

(57) ABSTRACT

A photopolymerization accelerator composition improving color stability and controlling polymerization shrinkage stress of cured resin and/or the resulting composite paste thereby feature by tertiary twisted biphenyldiamine with the general formula I:

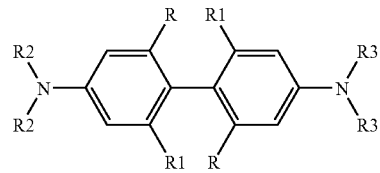

R2 and R3 are each independently alkyl having from 1 to 5 carbon atoms; R and R1 are each independently hydrogen or halogen; alkyl alkoxy, or alkylthio having from 1 to 18 carbon atoms; or phenyl and/or substituted phenyl alkoxy, or alkylthio having from 1 to 18 carbon atoms. It can be used in part with conventional photosensitizers and radically polymerizable monomers.

3 Claims, 2 Drawing Sheets

(58) Field of Classification Search
USPC .............. 522/65, 120, 28; 430/340; 106/35
See application file for complete search history.

(56) References Cited

U.S. PATENT DOCUMENTS

| | | |
|---|---|---|
| 4,287,083 A | 9/1981 | McDowell et al. |
| 4,366,228 A | 12/1982 | Specht et al. |
| 4,634,383 A | 1/1987 | Beyer et al. |
| 4,850,875 A | 7/1989 | Takatsu |
| 4,948,689 A * | 8/1990 | Kuroda ............... C09B 23/0091 430/58.15 |
| 5,166,177 A | 11/1992 | Thomas et al. |
| 5,344,916 A | 9/1994 | Harris et al. |
| 5,942,290 A | 8/1999 | Leppard et al. |
| 6,057,380 A | 5/2000 | Birbaum et al. |
| 6,191,191 B1 | 2/2001 | Harada et al. |
| 6,783,810 B2 | 8/2004 | Jin et al. |
| 7,544,721 B2 | 6/2009 | Gaud et al. |
| 2003/0116347 A1* | 6/2003 | Kubo et al. ............ 174/260 |
| 2004/0180983 A1 | 9/2004 | Hara et al. |
| 2004/0186195 A1 | 9/2004 | Suzuki et al. |
| 2004/0247889 A1* | 12/2004 | Nakajima et al. ......... 428/423.1 |

OTHER PUBLICATIONS

Murayama et al. JP 1994-107854 machine English translation (Apr. 1994).*

Murayama et al., machine English translation of JP 06-107854 (1994).*

* cited by examiner

Fig. 1: Molecular Structure of TMFBP

PHOTOPOLYMERIZABLE COMPOSITIONS FEATURING NOVEL AMINE ACCELERATOR FOR IMPROVED COLOR STABILITY AND REDUCED POLYMERIZATION STRESS THEREBY

BACKGROUND OF THE INVENTION

Light curable composition finds many applications in paints, coating, optical and microelectronic adhesives, dental adhesive and composites et al. UV and visible light are two common light sources to promote such curing reaction. Furthermore such a light curing process can also be classified as photo-induced cationic polymerization or photo-induced free radical polymerization based on the nature of photo-initiator and mechanism of polymerization. For any given light curable composition there is at least composed of a curable resin and photo-initiator. Typical curable resin include (meth)acrylate, vinyl, vinylether, epoxy, et al. Photo-initiators are photo-sensitizer, such as arylketone, diketone, acylphosphine oxide et al. Besides additional coinitiator or accelerator is also required in order to produce an effective curing. It has been found that tertiary aromatic amines, such as Ethyl-4-DimethylAmine Benzoate (EDAB), are the most effective accelerators. However, the accelerating efficiency between these tertiary aromatic amines depends heavily upon the substitution on the aromatic moiety. Moreover there is increasing concerns over the potential toxicity and the long-term effect on color stability for the resulting cured systems based on those conventional tertiary aromatic amines. It was believed color stability was influenced more by the nature of the aromatic ring than by the substituent on the nitrogen atom. Discoloration of the cured matrix containing such a tertiary aromatic amine is the increasing concern, especially when it is used as dental restoratives where color match is much more critical. Therefore there is a need for readily obtained, reactive, and color stable amine as novel photo coinitiator.

For dental application, it is more desirable to use photoinitiator which is color stable but demonstrate high ambient light (environmental light) stable and promote quick polymerization later on. Such a photoinitiator system composing an α-diketone, an aliphatic/aromatic amine and a triazane derivative, was disclosed in US Patent Application 2004/0180983. However, it is concerned about its potential problems in color stability and shrinkage stress concentration associated with for such a initiator system due to the nature of the isomerization nature of the triazine compound and the fast cure reaction rate.

One reason behind color shifting of cured dental resin and composite is attributed to the residual amine, which is generally a tertiary aromatic amine. UV or thermal aging can cause its isomerization to form colored structure. One solution to disrupt possible conjugation through such structural isomerization of aromatic moiety by making a substitute aromatic and isolated such aromatic ring. 2,2',6,6'-tetrasubstitute biphenyl have been explored to make colorless polymers.

Another issue associated with free radical-based light curing process is the shrinkage and shrinkage stress due to the fast curing nature of conventional free radical photopolymerization. Therefore there is need to develop new photo-initiator which can demonstrate good balance between quicker curing rate and lower curing stress for a novel free radical curing system. It is the intention for this invention is to further tune down the radical polymerization rate in an effort to reduce the shrinkage stress for a given cured composition.

It is well known that the origin of stress in adhesive resin composite restorations is due to the restrained shrinkage during polymerization and it is dependent on the configuration of the restoration. Moreover, non-homogeneous deformations during functional loading can damage the interface as well as the coherence of the material. Damage from these stresses can be reduced by application of elastic lining at the adhesive interfaces and by slowing the initial conversion by two-step light initiation of the resin. The various factors that mediate flow and compliance are all have something to do with polymerization stress buildup or failure of a restored tooth. In addition to the nature of resin composition, how a given resin or composite is cured is also critical to the total stress development, which means a kinetic control on the polymerization stress development is possible. With increasing MW, polymer chain mobility was limited, the diffusion become the rate control factor. In a comparison with linear system, the limited mobility in a cross-linking system appear to come earlier, which means extra reaction would lead to an increasing polymerization stress. Although such a cross-linking reaction could not allowed scarifying to exchange a low stress because it did contribute the mechanical property to the final material.

There are different approaches to control the stress generation and development:
1. Slow down the polymerization rate;
   Introducing a special rate controller like stable radicals or P&P resin system developed recently in this Company;
   Creating different polymerization zones from which the stress developed in a polymerized zone could be transferred to its adjacent unpolymerized zone and got relief like segmental polymerization technique developed in this company (U.S. Pat. No. 6,783,810);
   Employing different polymerization groups such as hybrid monomer with (meth)acrylate and vinyl ether.
   Using large-size macromonomer to limited its reactivity at the early stage;
2. Reduce the conversion;
   Pre-building a 2D or 3D structure like polymerizable macrocyclics developed in this Company, or dendremers or hyperbranches
3. Further tuning radical polymerization kinetic so as to allow stress relief during the course of cross-linking formation.

The present invention relates to a dental composite composition based on a novel tertiary aryl amine, more specifically a multiple, tertiary aryl amine which allow a better control over photopolymerization kinetics so as to generate much less curing contraction stress within a normal cross-linked system. In addition, composition from such novel amine can also offer improved color stability as comparison to that based on a conventional mono-tertiary aryl amine such as EDBA. Obviously the benefit from such a concept would not limit in dental composite or other dental materials. The application can be found in optical coating, microelectronic, et al.

SUMMARY OF THE INVENTION

The present invention is related to the use of a tertiary aromatic diamines as coinitiators or accelerator with conventional photoinitiator in light curable resin systems and/or any other resin compositions to reduce the discoloration of aromatic diamines in the said systems and to reduce the shrinkage stress from photopolymerization as well. More particularly, this invention relates to a class of tertiary aromatic diamines having twisted biphenyl moiety which not only demonstrate improved color stability of the resulting light curable resin and paste, but also offer reduced polymerization stress of the same resin and/or paste therefrom, which is highly desirable especially for dental restoratives.

Novel tertiary aromatic diamines containing twisted biphenyl moiety was initially designed for improved color stability for its usage as accelerator with alpha-diketone photoinitiator, such as camphorquinone. We have discovered that such tertiary aromatic diamines are very effective in improving color stability. Unlike prior tertiary aromatic amine used in dental formulation, such as EDAB, the tertiary aromatic amines of this invention contain twisted biphenyl moiety and multiple amine groups. Because of these multiple amine groups and its unique structure feature, the diamines of this invention are expected more susceptive to light-induced tautomerization or more stable than prior tertiary amines, which also results in a different photoreactivity as coinitiator.

We have also found that a distinguished photopolymerization kinetics of those resins or pastes from such new amine systems is demonstrated. Thus, another unique feature for those resin or paste containing such tertiary aromatic diamine can effectively reduce contraction stress via an effective stress dispersion through such extended network setting process. Furthermore, significantly improved color stability for those resin and/or paste composition which contain such a new amine have been demonstrated, even with higher amine content.

The monomer to be used in this invention may be any of monomers with at least one polymerizable olefinic unsaturated group. Among them, (meth)acrylate monomers are preferably used as the monomer. The (meth)acrylate monomer to be used preferably in this invention may be any of mono-functional (meth)acrylate monomers and polyfunctional (meth)acrylate monomers.

The preferable polymerizable composition for dental use may contain one or more the (meth)acrylate monomer described above so as to offer ultimate balanced overall performance, including mechanical strength, handling characteristics, improved color stability, reduced polymerization shrinkage and shrinkage stress.

DESCRIPTION OF RELATED ART

Aromatic tertiary amines have been widely used as coinitiator or accelerator for alpha-diketone-based photoinitiation system, which is usually in an amount of 0.01 to 5.0% by weight based on the amount of polymerizable resins. However, residual amine can cause an undesired color change, which would lead a color mismatch. In order to prevent the discoloration of cured systems, extra UV stabilizer such Uvinol has to be used in the composition in 0.5-2.0% wt/wt.

The use of photo stabilizers in any polymer matrix is well known in the art. These stabilizers are often used to protect the polymer or coating from the effects of heat, light, and ultraviolet radiation. Primary antioxidants, such as hindered phenolics, are often used to protect against oxidation at elevated temperatures. UV absorbers, such as the benzotriazoles, and hindered amine light stabilizers can be used to retard discoloration (yellowing) of cured polymers. Thus, it is desirable to develop a novel amine for replacing current EDAB so as to improve the color stabilization. Preferably, the new amine would prevent the discoloration of the aromatic diamine.

Figure 1:
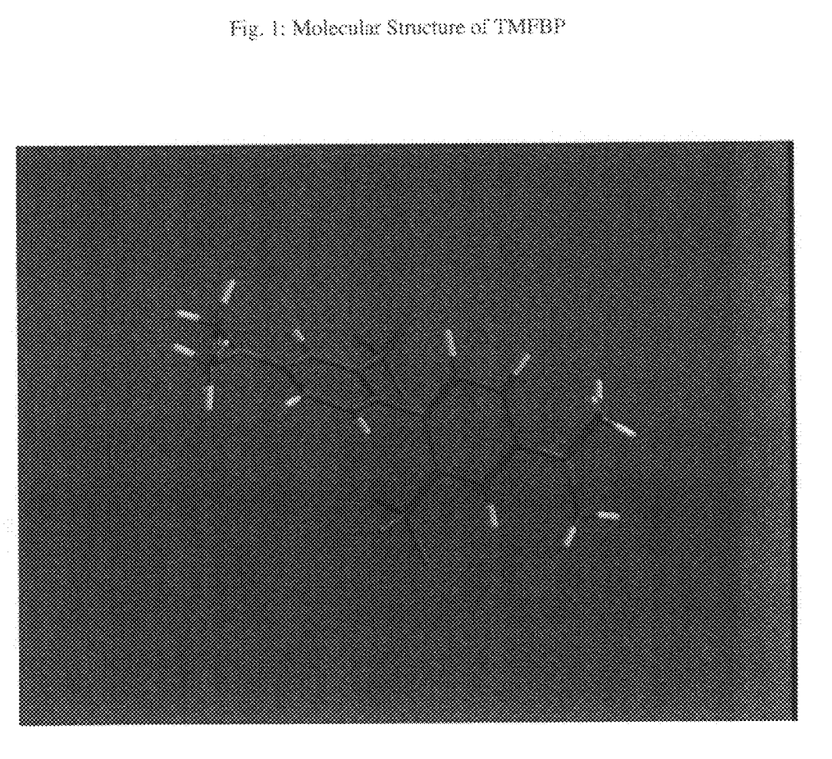
FIG. 1 shows the molecular structure of TMFBP.

Amine content is critical in balance of polymerization reactivity and storage stability. Increasing the concentration of EDAB will lead to the increasing reactivity, which would improve the mechanical strength and increase depth of cure, especially for dark shade. However, the down side for this is the increasing ambient light sensitivity and upcoming shade shift due to color instability of residual amine. It was believed that the oxidation of residual amine promotes a quinonoid formation, leading to color change. The new amine is based on a twisted biphenyl diamine, 2,2'-trifluoromethyl-4,4'-biphenyldiamine (TFMB). One-step methylation-reaction results in a tertiaryldiamine, N,N,N',N'-tetramethyl-2,2'-trifluoromethyl-4,4'-biphenyldiamine (TMFBP), see FIG. 1. It is expected such twisted amine would not only offer better solubility in resin system, but also demonstrate good color stability. On the other hand, it is also expected an unique reaction kinetics for such amine/resin system because of the featured diamine. TMFBP can be cored out for chain radiation growth unlike the one-way chain growth with a dead-end by any monoamine, such as EDAB.

As showed in Table I and Table II, new amine, TMFBP, was formulated with CQ/TPH resin and EDAB as control. Standard Harpoon filler formulation was used to make the composite pastes. Obviously, no significant difference between EDBA- and TMFBP-based resin and pastes was found for same amine level. However, the weak property from paste based on low level EDAB, LB5-188, suggested lower reactivity for that system as compared TMFBP system. More importantly, the accelerated aging test on the cured chips from neat resins, LB5-178-1 and LB5-178-2 vs. LB5-178-3 and LB5-178-4, showed that larger color shift (ΔE) was found for LB5-178-2 than LB5-178-4, 1.14 vs. 0.59. Extended aging test is in process. In addition, it was also noted that for same level CQ/EDAB and filler loading, TPH resin-based paste, LB5-188 still offer much higher shrinkage stress (2.6 MPa vs. 1.5 MPa) than those P&P-resin-based composite pastes as reported previously. The effect of new amine in P&P resin system will be investigated next.

Figure 2:
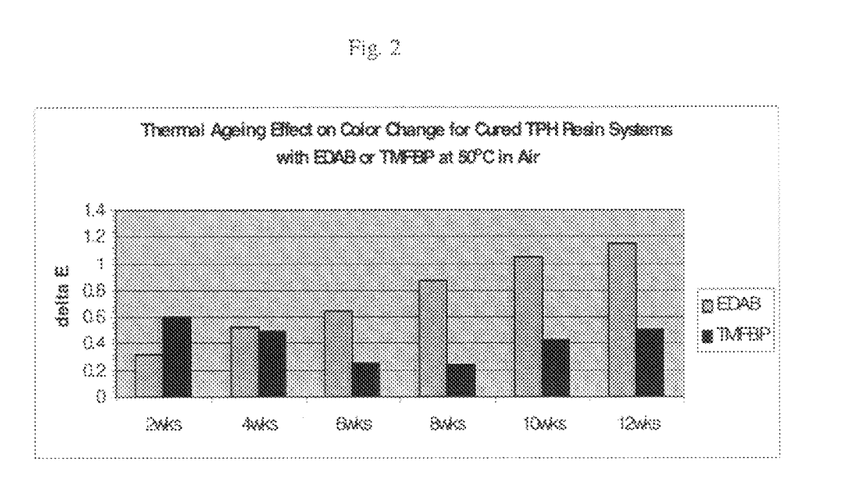
FIG. 2 is a table showing the thermal aging effect on color change for cured TPH resin systems with EDAB or TMFBP at 50° C. in air.
Figure 3:
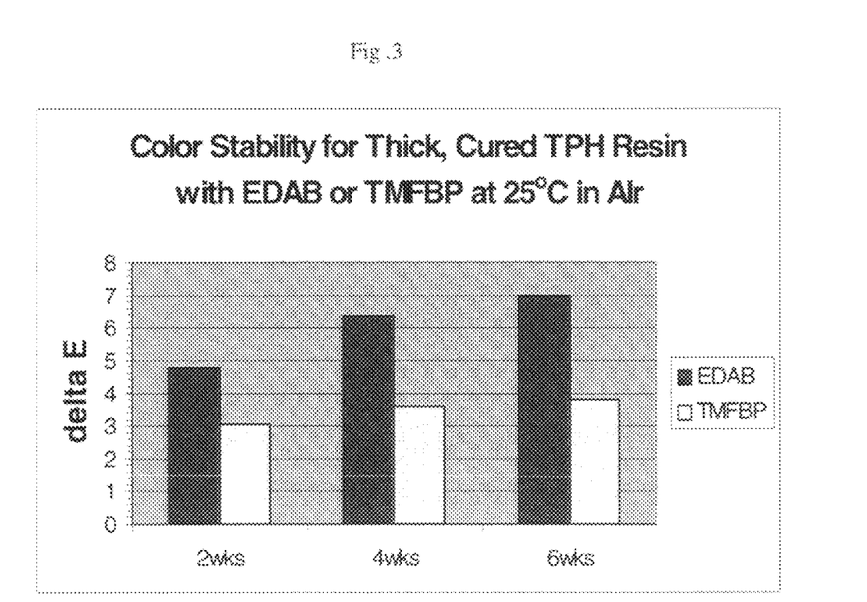
FIG. 3 is a table showing color stability for thick, cured TPH resin with EDAB or TMFBP at 25° C. in air.

To find out the last standing level for TMFBP in CQ/TPH resin system, a range of CQ/TMFBP composition was examined as showed in Table III and pastes were prepared accordingly (Table IV). Although there is no significant difference in polymerization shrinkage among these resin formulations, LB5-192-1, -2, -3, -4, -5, and -6, difference in shrinkage stress was revealed. Furthermore, there appears a critical amine level that governs the total shrinkage stress (FIG. 2). Similar effect of CQ on shrinkage stress was also noted, see FIG. 3. However, the significance of amine level on the shrinkage stress for the corresponding composite pastes was dimmed as showed in Table IV. Additional investigation is needed to identify the minimum TMFBP level in TPH resin system and to further evaluate the paste's color stability. A patent will be filled in this regard.

The invention will be further described in connection with the following examples that are set forth for purpose of illustration only.

EXAMPLE 1

Preparation of Tertiary Twisted Biphenyldiamine

As illustrated above, typical 2,2'-substituted biphenyl-N,N'-dimethyldiamine can be prepared directly from corresponding twisted diamines according to a procedure described in "Organic Synthesis, Coll. Vol. V, p 1084-87" for a mono-tertiarydiamine, m-Trifluoromethyl-N,N-dimethylamine. Similarly 2,2',6,6'-substituted biphenyl-N,N'-dimethyldiamine (see below) can prepared as well. However, other methods to prepare the twisted tertiary diamine with same or similar structure for same purpose in use will fall into the scope of this invention.

Scheme II: Chemical Structure illustration for Typical TetrasubstitutedTwisted Biphenyl Tertiary Diamines Add 28.6 grams (0.102 mole) of trimethyl phosphate into a 500 ml round-bottomed three-neck flask with a mechanical agitator, N2 inlet and a condenser. Then 21.4 grams (0.05 mole) of 2,2'-bis(trifluoromethyl)-biphenyl-4,4'-diamine (TFMB) was added into the system. Clear solution was soon developed and refluxed. The stirred reaction mixture was gradually heated by an oil bath to approximately 150 over 1-2 hrs, then the temperature has to be up to 200° C. so as to avoid the sublimation of the reactant in the flask. After 2-3 hrs, the reaction mixture is cooled to room temperature. Then a solution of 30 grams of NaOH in 200 ml of water is added to the flask with solidified reaction mixture and the mixture was carefully and vigorously stirred for 2 hrs. Insoluble crystalline solid is collected after filtration. Then it is recrystallized with acetone a couple of time. The structure of the resulting product is confirmed by NMR spectroscopy analysis (1H, F16 and C13).

EXAMPLE 2

Activated Resin Formulation with TFMBP

An activated resin mixture is prepared by mixing 30.0 grams of TPH resin, a mixture of EBPADMA and TEGDMA, 0.15 wt/wt % of CQ, 0.20 wt/wt % of TFMBP and 0.02 wt/wt % of BHT at 50.0° C. for 1 hr. Such an activated resin was thoroughly evaluated by polymerization shrinkage, shrinkage stress, conversion, and polymerization rate, which are summarized in Table I.

EXAMPLE 3

Light Curable Composite Containing TFMBP

The activated resin mixture as made above was then formulated into a composite paste with loading up to 82 wt/wt % of inorganic glass fillers as described elsewhere. Such paste was evaluated thoroughly as listed in table II.

COMPARABLE EXAMPLE 1

Activated Resin Formulation with EDAB

An activated resin mixture is prepared by mixing 30.0 grams of TPH resin, a mixture of EBPADMA and TEGDMA, 0.15 wt/wt % of CQ, 0.20 wt/wt % of EDAB and 0.02 wt/wt % of BHT at 50.0° C. for 1 hr. Such an activated resin was thoroughly evaluated by polymerization shrinkage, shrinkage stress, conversion, and polymerization rate, which are summarized in Table Ia and Ib.

EXAMPLE 2

Light Curable Composite Containing EDAB

It was then formulated into a composite paste with loading up to 82 wt/wt % of inorganic glass fillers as described elsewhere. Such paste was evaluated thoroughly as listed in table IIa and IIb.

TABLE Ia

Composition and Properties for Activated Resins with Different Amines

|  | 70% P&P Resin 15% TPH Resin 15% Diluent 147 0.15% CQ 0.20% EDAB | 70% P&P Resin 15% TPH Resin 15% Diluent 147 0.15% CQ 0.20% TMFBP | 85% P&P Resin 15% TEGDMA 0.15% CQ 0.20% EDAB | 85% P&P Resin 15% TEGDMA 0.15% CQ 0.20% TMFBP |
|---|---|---|---|---|
| Lot # | LB6-9-5 | LB6-9-2 | LB6-15-2 | LB6-15-1 |
| Viscosity@20° C. poise | 410 | 510 | 245 | 270 |
| Uncured density g/cm$^3$ | 1.1088 | 1.1087 | 1.1225 | 1.1231 |
| Cured density g/cm$^3$ | 1.1830 | 1.1826 | 1.2074 | 1.2086 |
| Shrinkage @ 24 hrs % | 6.27 | 6.25 | 7.03 | 7.07 |
| Stress @ 60 min MPa | 1.43 | 0.96 | 2.05 | 1.58 |
| $\Delta H_1$ in N2 w/o UV filter | 113 | 111 | 137 | 134 |
| $t_o$ seconds | 16.2 | 17.4 | 10.8 | 12.0 |
| $t_{max}$ seconds | 37.2 | 49.2 | 35.4 | 38.4 |
| $\Delta H_1$ in N2 w/ UV filter | 115 | 109 | 134 | 130 |
| $t_o$ seconds | 18.6 | 19.8 | 11.4 | 13.2 |
| $t_{max}$ seconds | 45.0 | 53.4 | 35.4 | 43.8 |

TABLE Ib

Composition and Properties for Activated Resins with Different Amines

|  | 100% P&P Resin 0.15% CQ 0.20% EDAB 0.02% BHT | 100% P&P Resin 0.15% CQ 0.20% TMFBP 0.02% BHT |
|---|---|---|
| Lot # | LB6-23-1 | LB6-23-2 |
| Viscosity@20° C. poise | 1550 | 1550 |
| Uncured density g/cm$^3$ | 1.1319 | 1.1326 |
| Cured density g/cm$^3$ | 1.2056 | 1.2059 |
| Shrinkage @ 24 hrs % | 6.11 | 6.08 |
| Stress @ 60 min MPa | 1.55 | 1.17 |
| $\Delta H_1$ in N2 w/o UV filter | 110 | 103 |
| $t_o$ seconds | 22.2 | 25.2 |
| $t_{max}$ seconds | 46.8 | 62.4 |
| $\Delta H_1$ in N2 w/ UV filter | 100 | 102 |
| $t_o$ seconds | 22.8 | 35.4 |
| $t_{max}$ seconds | 52.2 | 70.2 |

TABLE Ic

Amine Effect on Polymerization Stress for Comparable Resins

| Resins | w/ EDAB | w/ TMFBP | Stress Reduction, % |
|---|---|---|---|
| LB6-9-5 | 1.4 |  |  |
| LB6-9-2 |  | 1.0 | −29 |
| LB6-15-2 | 2.1 |  |  |
| LB6-15-1 |  | 1.6 | −24 |
| LB6-23-1 | 1.6 |  |  |
| LB6-23-2 |  | 1.2 | −25 |

TABLE Id

Effect of Initiator Composition on Polymerization Shrinkage and Stress for Activated TPH Resin

| Lot # | TPH Resin %, wt/wt | CQ %, wt/wt | TMFBP %, wt/wt | Shrinkage @ 24 hrs % | Stress @ 60 min MPa |
|---|---|---|---|---|---|
| LB5-192-1 | 100 | 0.10 | 0.10 | 7.14 | 3.0 |
| LB5-192-2 | 100 | 0.10 | 0.15 | 7.17 | 3.4 |
| LB5-192-3 | 100 | 0.10 | 0.20 | 7.11 | 3.7 |
| LB5-192-6 | 100 | 0.20 | 0.10 | 7.10 | 4.0 |
| LB5-192-4 | 100 | 0.20 | 0.20 | 7.22 | 4.2 |
| LB5-192-5 | 100 | 0.25 | 0.20 | 7.16 | 4.5 |

TABLE IIa

Composition and Properties for Composite with Different Amines

| | Pastes | | | |
|---|---|---|---|---|
| | LB6-14 | LB6-11 | LB6-17 | LB6-16 |
| Resins (composition) | LB6-9-5 18% | LB6-9-2 18% | LB6-15-2 17% | LB6-15-1 17% |
| Filler (Composition) | 82% | 82% | 83% | 83% |
| Uncured density g/cm$^3$ | 2.1469 | 2.1719 | 1.1852 | 1.1858 |
| Cured density g/cm$^3$ | 2.1752 | 2.1840 | 1.2205 | 1.2189 |
| Shrinkage @ 24 hrs % | 1.30 | 0.55 | 1.59 | 1.49 |
| Stress @ 60 min MPa | 1.34 | N/A | 1.70 | 1.50 |
| $\Delta H_1$ in N2 w/ UV filter | 21.8 | 19.8 | 21.0 | 19.6 |
| $t_o$ seconds | 12.0 | 12.0 | 15.6 | 18.6 |
| $t_{max}$ seconds | 44.4 | 49.2 | 52.8 | 65.4 |
| Flexural Strength MPa | 120 | N/A | 150 | 145 |
| Flexural Modulus MPa | 8300 | N/A | 10800 | 10300 |
| Compressive Strength MPa | 330 | 320 | 350 | 340 |
| Compressive Modulus MPa | 7600 | 7600 | 8000 | 7800 |

TABLE IIb

Composition and Properties for Composite with Different Amines

| | Pastes | |
|---|---|---|
| | LB6-24 | LB6-25 |
| Resins (Composition) | LB6-23-1 18% | LB6-23-2 18% |
| Filler (Composition) | 82% | 82% |
| Uncured density g/cm$^3$ | 2.1661 | 2.1660 |
| Cured density g/cm$^3$ | 2.1951 | 2.1926 |
| Shrinkage @ 24 hrs % | 1.32 | 1.21 |
| Stress @ 60 min MPa | 1.34 | 0.91 |
| $\Delta H_1$ in N2 w/ UV filter | 16.8 | 15.5 |
| $t_o$ seconds | 23.4 | 25.2 |
| $t_{max}$ seconds | 75.0 | 107.4 |
| Flexural Strength MPa | 138 | 137 |
| Flexural Modulus MPa | 11200 | 10000 |
| Compressive Strength MPa | 310 | 300 |
| Compressive Modulus MPa | 8000 | 8000 |

TABLE IIc

Amine Effect on Polymerization Stress for Comparable Pastes

| Pastes | EDAB | TMFBP | Stress Reduction, % |
|---|---|---|---|
| LB6-14 | 1.3 | | |
| LB6-11 | | na | na |
| LB6-17 | 1.7 | | |
| LB6-16 | | 1.5 | −12 |
| LB6-24 | 1.3 | | |
| LB6-25 | | 0.9 | −30 |

Thus, it should be evident that the invention as disclosed herein carries out one or more of the objects of the present invention set forth above and otherwise constitutes an advantageous contribution to the art. As will be apparent to persons skilled in the art, modifications can be made to the preferred embodiments disclosed herein without departing from the spirit of the invention, the scope of the invention herein being limited solely by the scope of the attached claims.

What is claimed is:

1. A photopolymerizable composition comprising an aromatic tertiary diamine having a twisted biphenyl moiety, a photosensitizer, and at least one polymerizable resin;

wherein the at least one polymerizable resin consists of at least one of a monofunctional (meth)acrylate monomer or a polyfunctional (meth)acrylate monomer; and wherein the aromatic tertiary diamine having the twisted biphenyl moiety is selected from the group consisting of:

-continued and combinations thereof.

2. A photopolymerizable composition comprising an aromatic tertiary diamine having a twisted biphenyl moiety, a photosensitizer, and at least one polymerizable resin; wherein the at least one polymerizable resin consists of at least one of a monofunctional (meth)acrylate monomer or a polyfunctional (meth)acrylate monomer; and wherein the aromatic tertiary diamine having the twisted biphenyl moiety comprises a trifluoromethyl substituent on each of the two phenyl groups in the twisted biphenyl moiety.

3. The composition of claim 2, wherein the aromatic tertiary diamine having the twisted biphenyl moiety comprises

* * * * *